(12) United States Patent
Pretzer et al.

(10) Patent No.: US 7,285,675 B2
(45) Date of Patent: Oct. 23, 2007

(54) N-HYDROXYALKYLTRIMELLITIMIDE ESTERS AND BIS-(TRIMELLITIMIDE) ESTERS AND METHOD OF MAKING

(75) Inventors: Wayne R. Pretzer, Wheaton, IL (US); Geraldine N. McDonald, Homer Glenn, IL (US)

(73) Assignee: Flint Hills Resources, S.a.r.l., Wichita, KS (US)

( * ) Notice: Subject to any disclaimer, the term of this patent is extended or adjusted under 35 U.S.C. 154(b) by 0 days.

(21) Appl. No.: 11/190,639

(22) Filed: Jul. 27, 2005

(65) Prior Publication Data
US 2007/0027292 A1 Feb. 1, 2007

(51) Int. Cl.
*C08G 69/26* (2006.01)
(52) U.S. Cl. ............... 558/272; 528/302; 528/310; 528/332; 528/422; 524/800; 524/802
(58) Field of Classification Search ........... 528/272, 528/302, 310, 332, 422; 524/800, 802
See application file for complete search history.

(56) References Cited

U.S. PATENT DOCUMENTS

| 3,060,191 | A |   | 10/1962 | Kolb et al. |
| 3,880,812 | A | * | 4/1975  | Golinkin et al. ............ 528/361 |
| 3,975,330 | A |   | 8/1976  | Suzuki et al. |
| 4,070,524 | A | * | 1/1978  | Keske ..................... 428/383 |
| 4,124,419 | A | * | 11/1978 | Keske ..................... 156/51 |
| 4,245,086 | A | * | 1/1981  | Uno et al. ................ 528/318 |
| 4,910,290 | A | * | 3/1990  | Tung et al. ............... 528/272 |
| 5,102,978 | A |   | 4/1992  | Richard et al. |
| 5,182,392 | A |   | 1/1993  | Tanisake et al. |

FOREIGN PATENT DOCUMENTS

| DE | 2659092 | 7/1997 |
| FR | 2376136 | 7/1978 |
| FR | 2435491 | 4/1980 |

\* cited by examiner

*Primary Examiner*—Duc Truong
(74) *Attorney, Agent, or Firm*—Clements Walker; Gregory N. Clements

(57) ABSTRACT

The present invention relates to trimellitic anhydride imide ester, a method of making it, and polyesters or polyamides that can be modified with trimellitic anhydride (TMA) to provide better heat resistance and mechanical properties. With the present invention, there are two processes for making TMA-ester. The first process is by charging into a reactor equimolar amounts of trimellitic anhydride and primary hydroxyalkylamine, primary carboxylalkylamine or primary carboxylarylamine, with an excess of alcohol or diol. The second process for producing the imide ester is to react two moles of TMA with one mole of a diamine of the formula $H_2N-X-NH_2$ with an excess of alcohol or diol; where X is an aliphatic, alicyclic, or aromatic group. Generally the reactor contains water as a dispersant for the reactants. The reaction time is from about 1-8 hours. The reaction temperature is from about 160° C. to about 220° C. After the cessation of water/alcohol production, the reaction is finished and the contents of the reactor can be cooled to cause the desired solid product to precipitate our. The solid is then separated by filtration or centrifugation.

13 Claims, No Drawings

N-HYDROXYALKYLTRIMELLITIMIDE ESTERS AND BIS-(TRIMELLITIMIDE) ESTERS AND METHOD OF MAKING

BACKGROUND OF THE INVENTION

1) Field of the Invention

The present invention relates to N-hydroxyalkyltrimellitimide esters and bis-(trimellitimide) esters, methods of making them, and polyesters or polyamides that can be modified with them to provide better heat resistance and mechanical properties. Specifically, the method of the present invention seeks to make N-hydroxyalkyltrimellitimide esters and bis-(trimellitimide) esters in one step. These products may then be reacted with polyester or polyamide to provide the desired properties mentioned above. With the present invention, N-hydroxyalkyltrimellitimide ester is made by charging into a reactor equimolar amounts of trimellitic anhydride and primary hydroxyalkylamine, primary carboxylalkylamine or primary carboxylarylamine, with an excess of alcohol or diol. Bis-(trimellitimide) ester is made by reacting two moles of TMA with one mole of a diamine of the formula $H_2N$—X—$NH_2$ with an excess of alcohol or diol; where X is an aliphatic, alicyclic, or aromatic group.

2) Prior Art

HETI TMA-Imide

Polyester, in which part of the monomers are replaced by N-hydroxyethyltrimellitimide (HETI) is reported to show increased heat resistance, hardness, and impact strength. The use of HETI in polyethylene terephthalate (PET) imparts superior mechanical properties and heat and fire resistance.

HETI is an imide prepared from trimellitic anhydride (TMA) and ethanolamine:

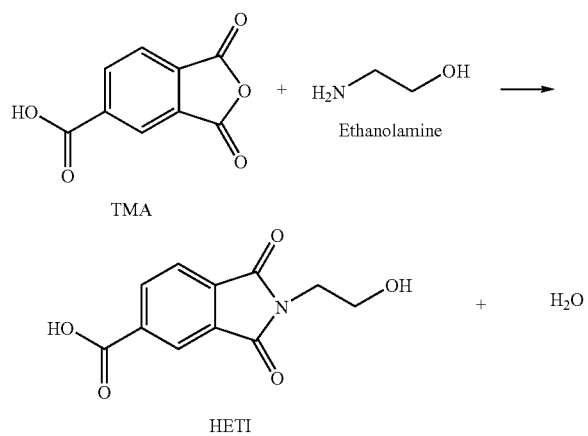

N-(Hydroxyethyl)trimellitimide possesses a primary hydroxyl group, and an aromatic carboxylic acid group. The aromatic imide group is known to be stable towards thermal and oxidative degradation. Generally, TMA and ethanolamine are reacted in a solvent at an elevated temperature and the product imide recovered by filtration. Methods vary depending on the specific reaction medium and the order of addition of the reactants (i.e., adding ethanolamine (sometimes referred to as monoethanolamine, $H_2N$—$CH_2$—$CH_2$—OH) to TMA or treating an ethanolamine solution with TMA).

It is also known to produce trimellitimide esters by first producing the imide and then converting the imide to an ester. This imide ester may then be reacted with or into polyester. The following prior art documents have been identified relative to the N-hydroxyalkyltrimellitimide ester and bis-(trimellitimide) ester process.

U.S. Pat. No. 3,060,191 to Kolb et al is drawn to a process of making trimellitic imides by reacting trimellitic anhydride with monoethanolamine (MEA). This new imide structure has a carboxyl group. The imide undergoes esterification and polycondensation to form modified polyester used to make fiber.

U.S. Pat. No. 3,975,330 to Suzuki et al discloses a process for making an imide modified polyester resin. The imide contains carboxyl groups. Esters are not mentioned. This reference does mention blending imides with polyesters.

U.S. Pat. No. 4,245,086 to Uno et al discloses a process for making trimellitic imide by reacting trimellitic anhydride with a monoalkylamine such as MEA, in the presence of specified catalysts. Two examples also show the preparation of a modified polymer by reaction of a HETI pre-polymer with bis-β-hydroxyethyl terephthalate (i.e. the precursor to PET). These compositions contain only a small amount of PET (2-4%). All the imides formed under the production process outlined in this patent have carboxyl groups.

U.S. Pat. No. 4,910,290 to Tung et al discloses that mechanical and thermal properties of polyester can be improved by incorporating trimellitic imides therein. More specifically, the imide is copolymerized into the polyester as a monomeric repeating unit. This patent discloses first making a trimellitic imide, then making a PET oligomer, and then reacting the imide with the oligomer in a copolymerization process. The polyester comprises 5-80 wt. % imide. Examples show preparation of modified PET compositions by heating PET oligomer and hydroxyethyl trimellitic imide (HETI) in the presence of antimony catalyst. The modified polyesters had better thermal properties compared to the control PET as shown by higher glass transition temperatures.

U.S. Pat. No. 5,102,978 to Richard et al discloses a typical imide with carboxyl end groups. The imide can be blended with polyester to create desired properties. The polyester most frequently mentioned is PET. The imide can be an imide-containing diacid monomer or diester thereof. Specifically, Example 1 teaches terephthalic acid and ethylene glycol are first condensed to a PET oligomer (PET heel), and then you react trimellitic anhydride (TMA) with various diamines to create bis-(trimellitimide) diacids. These diacids are then reacted with or copolymerized with polyethylene terephthalate oligomers.

U.S. Pat. No. 5,182,392 to Tanisake et al discloses a process for producing a bis-(trimellitimide) having carboxyl end groups. No imide esters are disclosed and there is no disclosure for reacting the imide with polyester.

French patent 2,435,491 to Toyo Boseki discloses a process for preparing imides by reacting trimellitic anhydride with a monoalkylamine. The production of the imide is carried out in various solvents including ethylene glycol. However, there is no disclosure of this being an imide ester product.

French patent 2,376,136 discloses a process for reacting trimellitic anhydride with a monoalkylamine. Again, various solvents are mentioned, including ethylene glycol and diethylene glycol.

German patent 2,659,092 to Toyo Boseki likewise teaches reacting trimellitic anhydride with a monoalkanolamine. There is no disclosure of reacting the imide with polyester.

The prior art discloses making a functional (carboxyl or hydroxyl) trimellitimide, making polyester oligomers, and then copolymerizing the imide with the oligomers. The imides are typically in powder form and are not easily copolymerized with polyester. Furthermore, the imides react or condense with themselves and thus have a tendency to not totally react with the polyester.

In the prior art set forth above, there was a disclosure for making trimellitic imides, a disclosure of reacting such imides with polyester, but no disclosure of a one-step process for making the trimellitimide esters. There is a need to make N-hydroxyalkyltrimellitimide esters and bis-(trimellitimide) esters that are easily blended with and compatible with polyester. There is a need to make N-hydroxyalkyltrimellitimide ester and bis-(trimellitimide) ester modified polyester to provide better heat resistance and mechanical properties.

SUMMARY OF THE INVENTION

The inventors have found that they can produce a N-hydroxyalkyltrimellitimide ester or bis-(trimellitimide) ester directly in a one step process (by two different methods), and that this product is compatible with the monomers used in making PET, thus forming copolyesters. The present invention seeks to produce a N-hydroxyalkyltrimellitimide ester or bis-(trimellitimide) ester because it has a relatively low melt temperature (compared to the high melting, carboxyl functional, powder imides) and can be added as a liquid or melt into the liquid monomer during the production process of the polyester, and particularly at the polycondensation polymerization step.

More specifically, the inventors invented a process for making N-hydroxyalkyltrimellitimide ester and another process for making bis-(trimellitimide) ester.

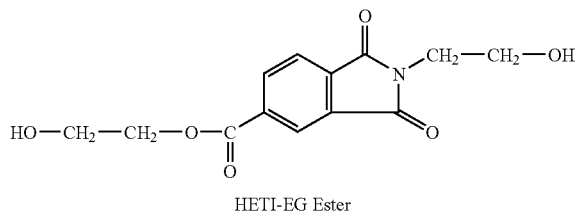

HETI-EG Ester

The first inventive process for making N-hydroxyalkyltrimellitimide ester can produce, for example, N-hydroxyethyltrimellitimide ethylene glycol ester (also known as HETI-EG ester) from a single reaction between TMA, monoethanolamine, and an excess of EG. The second inventive process for making bis-(trimellitimide) ester can produce bis-(trimellitimide)-bis ethylene glycol ester from a single reaction between TMA, a diamine and an excess of EG. The diamine is of the formula $H_2N$—X—$NH_2$ where X is an aliphatic, alicyclic, or aromatic group.

The HETI-EG ester process produces a product that is a mixture of HETI-EG and HETI-EG derivatives. Typically, this mixture comprises about 78-90% HETI-EG ester, 8-15% $(HETI)_2$-EG ester, 0.5-3.0% $(HETI)_3$-EG ester, 0.1-0.5% $(HETI)_4$-EG ester, 0.5-1.5% HETI, 0.1-0.5% $(HETI)_2$, and 0.5-2.5% other HETI containing molecules. This product mixture is useful for the modification of polyesters such as PET and it also has utility in modification of other condensation polymers such as polyamides.

In the broadest concept, the present invention relates to a process for the production of N-hydroxyalkyltrimellitimide ester (such as HETI-EG) comprising: reacting equimolar amounts of trimellitic anhydride, primary amine, and an excess of alcohol, or diol, or both, wherein the primary amine is selected from hydroxyalkylamine, carboxyalkylamine, carboxyarylamine, or a mixture of these.

In the broadest concept, the present invention relates to a process for the production of bis-(trimellitimide) ester, comprising: reacting a 2:1 molar ratio of trimellitic anhydride and a diamine, and an excess of alcohol, or diol, or both, wherein said diamine is of the formula $H_2N$—X—$NH_2$, and X is selected from aliphatic, alicyclic, aromatic, or a mixture of these.

In the broadest scope of the present invention, the product from either of the two methods of making the trimellitimide or bis-(trimellitimide) ester is contemplated and any copolymers made with polyester(s) or polyamide(s).

DESCRIPTION OF THE PREFERRED EMBODIMENTS

The product of the present invention is a trimellitimide ester. Specifically, the trimellitimide esters are N-hydroxyalkyltrimellitimide-esters and bis-(trimellitimide) esters. For example, 4-(2-hydroxyethoxycarbonyl)-N-hydroxyethyltrimellitimide, is an aromatic imide ester possessing two hydroxyethyl groups and no carboxyl groups. There are two different reactions that can produce N-hydroxyalkyltrimellitimide-ester and bis-(trimellitimide) ester. These esters do not condense with themselves, melt at a relatively low temperature, and can be added as a liquid modifier into a polyester polymerization.

The inventors have found surprisingly that N-hydroxyalkyltrimellitimide esters and bis-(trimellitimide) esters are formed as the major products by charging/reacting in a single reactor either: 1) equimolar amounts of TMA and a primary hydroxyalkylamine, primary carboxyalkylamine, primary carboxyarylamine, or a mixture of these, and an excess of alcohol or diol, or 2) a 2:1 molar ratio of TMA and a diamine of formula $H_2N$—X—$NH_2$ (X is an aliphatic, alicyclic, or aromatic group) and an excess of alcohol or diol. Water can be added to assist in the dispersion and dissolution of the reactants. The reactor contents are heated with agitation under a blanket of nitrogen and water (or alcohol, when an excess of alcohol is used instead of the diol) is removed overhead as the reactor temperature rises above 100° C. Reaction temperature is raised to about 180-200° C. (160-220° C.). Typically, the reactor contents become clear and homogeneous during heating. Heating of the reaction mixture is continued until the reaction is complete, typically 0.5-2 hours (0.25-6 hours) after evolution of water (or alcohol) has stopped. The product precipitates as the reaction mixture is cooled (e.g. to around 0° C.). Precipitation also can be initiated by the addition of a medium that is a poor solvent for the products (e.g. water or methanol) and/or introduction of seed material (e.g. ester product made previously). A combination of these techniques is sometimes most effective. The solid product can be collected by filtration or centrifugation. The product can be further washed with a poor solvent to remove traces of the excess alcohol or diol adhering to the product.

The primary hydroxyalkyl amine component utilized in the present invention will be normally selected from the group consisting of primary amine alcohols containing 2 to 12 carbon atoms. Typical suitable primary hydroxyalkyl amines are: monoethanolamine; 2-amino-1-propanol;

3-amino-1-propanol; 2-amino-2-propanol; 1-amino-2-porpanol; 2-amino-1-butanol; 4-amino-1-butanol; 2-amino-2-methyl-1-propanol; 5-amino-1-pentanol; 2-amino-1-pentanol; 2-amino-3-methyl-1-butanol; 3-amino-2,2-dimethyl-1-propanol; 6-amino-1-hexanol; 2-amino-1-hexanol; 2-amino-3,3-dimethyl-1-butanol; 2-amino-4-methyl-1-pentanol; 2-amino-3-methyl-1-pentanol; 7-amino-1-heptanol; 5-amino-2,2-dimethylpentanol; 8-amino-1-octanol; 6-amino-2-methyl-2-heptanol; 4-amino-cyclohexanol; 1-amino-1-cyclopentanemethanol; 4-aminocyclohexanemethanol; 2-phenylglycinol.

The primary carboxyalkyl amine component utilized in the present invention will be normally selected from the group consisting of primary amino carboxylic acids containing 2 to 12 carbon atoms. Typical suitable carboxyalkyl amines are: glycine; 2-aminopropionic acid; 3-aminopropionic acid; 2-aminobutanoic acid; 3-aminobutanoic acid; 4-aminobutanoic acid; 2-aminoisobutyric acid; 2-aminopentanoic acid; 2-amino-3-methylbutanoic acid; 5-aminopentanoic acid; 6-aminohexanoic acid; 2-amino-3-methylpentanoic acid; 2-amino-4-methylpentanoic acid; 2-amino-3,3-dimethylbutanoic acid; 7-aminoheptanoic acid; 1-aminocyclohexanecarboxylic acid; 4-aminocyclohexanecarboxylic acid; 4-aminophenylacetic acid; 3-aminophenylacetic acid; 2-aminophenylacetic acid; phenylglycine; phenylalanine, 3-(4-aminophenyl)propionic acid.

The primary carboxyaryl amine component utilized in the present invention will be normally selected from the group consisting of primary amino aromatic carboxylic acids containing 7 to 16 carbon atoms. Typical suitable carboxyaryl amines are: 4-aminobenzoic acid; 3-aminobenzoic acid; 3-amino-4-methylbenzoic acid; 4-amino-3-methylbenzoic acid; 3-amino-2-methylbenzoic acid; 4-(aminomethyl)benzoic acid; 4-(2-aminoethyl)benzoic acid; 6-amino-2-naphthoic acid; 3-amino-2-naphthoic acid.

The diol component utilized in the present invention will be normally selected from the group consisting of diols containing 2 to 12 carbon atoms, glycol ethers containing from 3 to 12 carbon atoms and polyether glycols. Typical diols suitable for the present invention are: ethylene glycol; diethylene glycol; 1,3-propanediol, 1,2-propylene glycol; 2,2-dimethyl-1,3-propanediol; 2-ethyl-2-butyl-1,3-propanediol; 1,3-butanediol; 1,4-butanediol; 1,6-hexanediol; 1,4-cyclohexanedimethanol; 1,3-cyclohexanedimethanol; 2,2,4-trimethyl-1,6-heaxanediol.

The alcohol component utilized in the present invention will be normally selected from the group consisting of alcohols containing 1 to 12 carbon atoms and monoesters and monoethers of glycols containing 3 to 12 carbon atoms. Typical alcohols suitable for the present invention are: methanol, ethanol, 1-propanol, 2-propanol, 1-butanol, 2-butanol, tert-butyl alcohol; iso-butyl alcohol; 1-hexanol; cyclohexyl alcohol; 1-octanol; 2-ethylhexanol; iso-octanol; iso-nonyl alcohol; benzyl alcohol; ethylene glycol monomethyl ether; ethylene glycol monoethyl ether; ethylene glycol monobutyl ether; ethylene glycol monoacetate; diethylene glycol monomethyl ether; diethylene glycol monoethyl ether.

The primary diamine component utilized in the present invention will be normally selected from the group consisting of primary aliphatic and aromatic diamines containing 2 to 16 carbon atoms. Typical suitable diamines are: ethylenediamine; trimethylenediamine, tetramethylenediamine; pentamethylenediamine; hexamethylenediamine; heptamethylenediamine; octamethylenediamine; 1,4-diaminocyclohexane; 1,4-bis(aminomethyl)cyclohexane; bis-(4-aminocyclohexyl)methane; isophoronediamine; meta-xylylenediamine; para-xylylenediamine; 4,4'-diaminodiphenylmethane; 4,4'-diaminobiphenylpropane; 4,4'-diaminodiphenylsulfone; m-phenylene diamine; p-phenylenediamine; 2,6-diaminonaphthalene; 1,5-diaminonaphthalene.

Although the utility of the present invention is described in terms of making a copolymer based on trimellitimide ester and polyester, other polycondensation polymers/copolymers are within the scope of the invention. Suitable polyesters are polyethylene terephthalate (PET), polybutylene terephthalate (PBT), poly(trimethylene) terephthalate (PTT), polyethylene isophthalate (PEI), polyethylene naphthalate (PEN), and copolymers based on these. Other polycondensation polymers are polyamides such as nylon 6, nylon 6/6, nylon 6/10, nylon 11, nylon 12, nylon 6/12, nylon 10/12, nylon 4/6, nylon 6/9, and aramides such as poly(m-phenylene iso-phthalamide), poly(p-phenylene ter-phthalamide), poly(phthalamide), and copolymers based on these.

The following Examples are to assist in the understanding of the invention, but are not intended to limit the invention beyond the scope of the claims. Analyses using $^1$H NMR (proton nuclear magnetic resonance) were conducted at ambient temperature (about 26° C.) using deuterated DMSO (dimethyl sulfoxide) solvent. High pressure liquid chromatography (HPLC) was performed using a Waters 300×3.9 mm NovaPak C18 column. The mobile phase components were 0.5% formic acid in water and acetonitrile. Gradient elution was employed and peak elution time and size was determined by measuring signal strength at 229 nm.

EXAMPLE 1

A 1-liter, glass resin kettle equipped with an overhead stirrer, steam-cooled condenser, water cooled condenser, nitrogen inlet and outlet, addition funnel, thermocouple, and external heating mantel was charged with 192.1 grams (1 mole) of trimellitic anhydride (TMA) and purged with nitrogen. About 300 ml of deionized water were then added to the kettle and stirring initiated. Monoethanolamine (MEA), 62.09 grams (1 mole), was added drop wise via the addition funnel over the span of about 5 minutes. The reaction mixture was heated to about 80° C. and 68.5 grams (1.1 moles) of ethylene glycol (EG) added. The stirred mixture was heated to 120° C. over about 2.5 hours and an additional 375 grams (6.04 moles) of EG charged. The reactor contents formed a clear solution during this time and water was collected overhead. The stirred reaction solution was slowly heated to 180° C. over an additional period of 2.25 hours, held at 180° C. for 1 hour, and then allowed to cool to room temperature. The light yellow product solution was combined with about 352 ml of water. The resultant white precipitate was collected by filtration to yield 395 grams of unwashed product. The product was washed twice with about 500 ml of warm (35-40° C.) water. The product was collected by filtration and dried at 50° C. About 116 g of product was obtained. Analysis of this material by $^1$H NMR (Proton Nuclear Magnetic Resonance) shows a composition comprising about 17% HETI-EG ester and 83% HETI (excluding any water and ethylene glycol still present). Analysis by LC (Liquid Chromatography) shows about 28% HETI-EG ester products and 66% HETI.

These LC analyses easily separate all the reaction components, but do not use individual response factors for each species detected and relative amounts reported should be interpreted carefully. Relative distribution of chemically similar species will be more accurate than comparing distinctly unlike molecules. NMR analyses will be more accurate quantitatively, but cannot easily distinguish the various HETI-ester species.

EXAMPLE 2

A 1-liter, glass resin kettle equipped with an overhead stirrer, steam-cooled condenser, water cooled condenser, nitrogen inlet and outlet, addition funnel, thermocouple, and external heating mantel was charged with 192.2 grams (1 mole) of TMA and purged with nitrogen. About 300 ml of deionized water were then added to the kettle and stirring initiated. MEA, 62.09 grams (1 mole), was added drop wise via the addition funnel over the span of about 5 minutes. The funnel was rinsed with 30 ml of water and the rinse was added to the reactor. The reaction mixture was heated to about 80° C. and 68.4 grams (1.1 moles) of EG added together with 20 ml of water used to rinse the addition funnel. The stirred mixture was heated to 120° C. over about 2.5 hours and an additional 373.6 grams (6.02 moles) of EG charged. The reactor contents formed a clear solution during this time and water was collected overhead. The stirred reaction solution was slowly heated to 200° C. over an additional period of 2.75 hours, held at 200° C. for 1.8 hours, and then allowed to cool to room temperature. The bright yellow solution was cooled to about 0° C. The white precipitate that formed was collected by filtration in four portions. The first three portions gave 92.7 grams of unwashed product. Analyses by $^1$H NMR and HPLC (high pressure liquid chromatography) showed that this material comprised about 66% HETI ester, 6% HETI/HETI ester derivatives, and 28% ethylene glycol. The fourth portion of precipitate was washed three times with cold methanol (about 0° C., 800 ml total) and yielded 18.3 grams of white powder.

EXAMPLE 3

A 1-liter, glass resin kettle equipped with an overhead stirrer, steam-cooled condenser, water cooled condenser, nitrogen inlet and outlet, addition funnel, thermocouple, and external heating mantel was charged with 192.1 grams (1 mole) of TMA and purged with nitrogen. About 300 ml of deionized water were then added to the kettle and stirring initiated. MEA, 62.1 grams (1 mole), was added drop wise via the addition funnel over the span of about 5 minutes. The funnel was rinsed with 30 ml of water and the rinse was added also to the reactor. The reaction mixture was heated to about 80° C. and 68.4 grams (1.1 moles) of EG added. The stirred mixture was heated to 120° C. over about 2 hours. The reactor contents formed a clear solution during this time and water was collected overhead. After about 300 ml of water was collected, an additional 371 grams (6.0 moles) of EG was charged. The stirred reaction solution was heated to 200° C. over an additional period of 2 hours, held at 200° C. for 3.75 hours, and then allowed to cool to room temperature. The bright yellow solution was cooled to about 0° C. A white precipitate formed that was collected by filtration in four, approximately equal, portions. The solid collected from each portion was washed twice with about 30 ml of cold (0° C.) methanol. The combined product was 154.9 grams. Analysis by $^1$H NMR showed this material comprised about 86% HETI-ester, 5% HETI/HETI-ester derivatives, and 9% ethylene glycol.

EXAMPLE 4

A 1-liter, glass resin kettle equipped with an overhead stirrer, steam-cooled condenser, water cooled condenser, nitrogen inlet and outlet, addition funnel, thermocouple, and external heating mantel was charged with 192.1 grams (1 mole) of TMA and purged with nitrogen. About 300 ml of deionized water were then added to the kettle and stirring initiated. MEA, 62.1 grams (1 mole), was added drop wise via the addition funnel over the span of about 5 minutes. The funnel was rinsed with 30 ml of water and the rinse was added also to the reactor. The reaction mixture was heated to about 90° C. and 69.8 grams (1.1 moles) of EG added. The stirred mixture was heated to 120° C. over about 2.8 hours. The reactor contents formed a clear solution during this time and about 280 ml of water was collected overhead. An additional 370 grams (6.0 moles) of EG was then charged. The reactor was maintained at 80° C. overnight (about 14 hours). On the following morning, the stirred reaction solution was heated to 200° C. over a period of 3 hours, held at 200° C. for 6 hours, and then allowed to cool to room temperature. The bright golden solution was cooled to about 0° C. A white precipitate formed. The mixture was filtered in about five equal portions. The product from each portion was washed twice with approximately 30 ml of cold methanol (0° C.). Recovery was about 222.3 grams of white crystalline product. Analysis by $^1$H NMR showed that the material comprised about 75 wt. % HETI-ester, 4% HETI/HETI-ester derivatives, and 21% EG.

EXAMPLE 5

A 1-liter, glass resin kettle equipped with an overhead stirrer, steam-cooled condenser, water cooled condenser, nitrogen inlet and outlet, addition funnel, thermocouple, and external heating mantel was charged with 192.2 grams (1 mole) of TMA and purged with nitrogen. About 300 ml of deionized water were then added to the kettle and stirring initiated. MEA, 62.1 grams (1 mole), was added drop wise via the addition funnel over the span of about 15 minutes. The funnel was rinsed with 30 ml of water and the rinse was added also to the reactor. The reaction mixture was heated to about 80° C. and 438.4 grams (7.1 moles) of EG added. The stirred mixture was slowly heated to 200° C. over about 5.5 hours. The reactor contents formed a clear, pale yellow solution during this time and about 360 ml of water was collected overhead. The reactor was held at 200° C. for 3.8 hours and then allowed to cool to room temperature. A white precipitate formed after standing at room temperature several days. The entire reaction mixture was then cooled to 0° C. and filtered in several portions. Each portion collected was washed twice with cold (0° C.) methanol. The solid was dried in air overnight. The total amount of product collected was 190.5 grams. Analysis of this product by $^1$H NMR gave a composition comprising about 7 wt. % EG, 86% HETI-ester products, and 7% HETI.

Analysis by 1H NMR of the room temperature, final reaction mixture before the onset of precipitation showed a composition comprising about 55 wt. % EG, 42% HETI-ester products, and 3% HETI.

EXAMPLE 6

A 1-liter, glass resin kettle equipped with an overhead stirrer, steam-cooled condenser, water cooled condenser, nitrogen inlet and outlet, addition funnel, thermocouple, and external heating mantel was charged with 192.2 grams (1 mole) of TMA and purged with nitrogen. About 300 ml of deionized water were then added to the kettle and stirring initiated. MEA, 62.1 grams (1 mole), was added drop wise via the addition funnel over the span of about 13 minutes. The funnel was rinsed with 40 ml of water and the rinse was added also to the reactor. The reaction mixture was heated to about 80° C. and 438.5 grams (7.1 moles) of EG added. The stirred mixture was slowly heated to 180° C. over about 5 hours. The reactor contents formed a clear, pale yellow solution during this time and about 355 ml of water was collected overhead. The reactor was then allowed to cool to about 80° C. overnight. The reactor contents were heated to 200° C. on the following morning. The reactor was held at 200° C. for about 4 hours during which time an additional 10 ml of water were collected and then allowed to cool. About 200 ml of chilled water (about 0° C.) were added to the reactor when the contents had cooled to around 46° C. White, solid HETI-ester (7.6 grams) was then added with stirring when the reactor contents reached about 30° C. The reactor was immersed in ice water for about an hour. White precipitate formed and was collected by filtration. The precipitate was washed twice on the filter with chilled methanol (0° C.). The product was dried overnight at room temperature. About 232 grams were isolated.

Analysis by 1H NMR of the washed and dried product showed a composition comprising about 75 wt. % HETI-ester products, 14% EG, 7% methanol, and 4% HETI.

EXAMPLE 7

A 1-liter, glass resin kettle equipped with an overhead stirrer, steam-cooled condenser, water cooled condenser, nitrogen inlet and outlet, addition funnel, thermocouple, and external heating mantel was charged with 192.2 grams (1 mole) of TMA and purged with nitrogen. About 300 ml of deionized water were then added to the kettle and stirring initiated. MEA, 62.1 grams (1 mole), was added drop wise via the addition funnel over the span of about 10 minutes. The funnel was rinsed with 30 ml of water and the rinse was added also to the reactor. The reaction mixture was heated to about 80° C. and 253 grams (4.1 moles) of EG added. The reaction mixture was clear and colorless. The temperature was slowly raised to 200° C. over 8 hours. About 345 ml of water were collected during this time. The reactor was maintained at 200° C. for 3 hours. An additional 5 ml of water were collected and the reaction solution became bright yellow and finally amber yellow. The temperature of the reactor was allowed to cool to 80° C. and then 200 ml of chilled water were added to the reaction kettle. The reaction solution became hazy. The kettle was immersed in ice water and a white precipitate began to form after about 30 minutes. The product was filtered and washed twice with cold (0° C.) methanol. The product was dried overnight at 55° C. Final weight was 215.4 grams of an off-white solid. About 63 grams of this product was washed with about 180 ml methanol and product collected by filtration.

EXAMPLE 8

A 1-liter, glass resin kettle equipped with an overhead stirrer, steam-cooled condenser, water cooled condenser, nitrogen inlet and outlet, addition funnel, thermocouple, and external heating mantel was charged with 438 ml (488.6 grams, 7.87 moles) of ethylene glycol and 192.2 grams (1 mole) of TMA. The reactor was purged with nitrogen and stirring initiated. A mild exotherm was observed and the contents were stirred for about 2 hours. MEA, 61.0 ml (62.1 grams, 1 mole), was added drop wise via the addition funnel over the span of about 15 minutes. The reaction mixture was slowly heated to 200° C. over several hours and then maintained at 200° C. for about 4 hours. About 37 ml of water were collected and the reaction solution became yellow and clear. Heating was discontinued and the reactor contents were allowed to cool to about 40° C. About 5 grams of HETI-EG ester prepared previously was then added to the reactor and the mixture stirred slowly for 5-10 minutes. The contents became cloudy after about 15 minutes. Precipitation was complete after about 30-45 minutes during which time a thick, white semisolid mixture formed. The product was washed twice with cold (3° C.) water, filtered, and dried.

EXAMPLE 9

A 1-liter, glass resin kettle equipped with an overhead stirrer, steam-cooled condenser, water cooled condenser, nitrogen inlet and outlet, addition funnel, thermocouple, and external heating mantel was charged with 900 ml (1,004 grams, 16.2 moles) of ethylene glycol and 192.0 grams (1 mole) of TMA. The reactor was purged with nitrogen and stirring initiated. MEA, 62.1 grams (1 mole), was added drop wise via the addition funnel over the span of about 10 minutes. An exotherm was observed that raised the temperature of the reactor contents to about 58° C. The reaction mixture was slowly heated to 200° C. over 3.5 hours and then maintained at 200° C. for about 5 hours. About 35 ml of water were collected and the reaction solution became golden yellow and clear. Heating was discontinued and the reactor contents were allowed to cool to about 40° C. About 5 grams of HETI-EG ester prepared previously was then added to the reactor and the mixture stirred slowly for 5-10 minutes. Stirring was then stopped. Precipitation was complete after about 30-45 minutes during which time a thick, white semisolid mixture formed. The product was collected by vacuum filtration. About 197 grams of crude product was obtained. The crude product was stirred with about 1400 ml of cold (0° C.) water and filtered to obtain about 177 grams of washed product.

COMPARATIVE EXAMPLE A

Ethylene glycol (EG) and HETI in a 1.05:1 molar ratio (EG:HETI) were charged to a round-bottom flask fitted with an air-cooled vigreux column, nitrogen inlet, thermocouple and mechanical stirrer. The EG was first charged to the flask followed by the HETI. The flask was then purged with nitrogen. The mixture was heated to 190-195° C. to minimize EG reflux and achieve better separation of EG from water in the fractionation column. A slight purge of nitrogen was maintained to the flask over the course of reaction. The reaction with EG occurs fairly rapidly once the temperature exceeds 180° C. The reaction was held at temperature for ~3 hrs. and a pale yellow solution formed. The contents were cooled to room temperature. A glassy, pale-yellow solid was obtained. The product comprised only about 34.5% HETI-EG ester. Most of the other products were higher HETI condensation products, e.g. HETI condensed with HETI-EG ester, 2 HETI condensed with HETI-EG ester, HETI condensed with HETI, etc.

COMPARATIVE EXAMPLE B

The procedure described in Comparative Example A was repeated except that the mole ratio of EG to HETI was 10:1. After about 3 hours at 190-200° C., the yellow reaction solution was cooled to room temperature. A white precipitate formed after standing for several hours. The precipitate was collected by filtration and washed with cold (about 0° C.) water. The product composition was determined by LC analysis. The product comprised about 81.9% HETI-ester and <16.5% higher condensation products.

COMPARATIVE EXAMPLE C

A 1-liter, glass resin kettle equipped with an overhead stirrer, steam-cooled condenser, water cooled condenser, nitrogen inlet and outlet, addition funnel, thermocouple, and external heating mantel was charged with 192.2 grams (1 mole) of TMA and purged with nitrogen. About 300 ml of deionized water were then added to the kettle and stirring initiated MEA, 62.1 grams (1 mole) was added drop wise via the addition funnel over the span of about 25 minutes. The funnel was rinsed with 50 ml of water and the rinse was added also to the reactor. The reaction mixture was heated to about 95° C. After about 5 hours, a white precipitate began to form and 70.4 g (1.05 moles) of (EG added. The reaction mixture became clear and colorless. The temperature was slowly raised to 190° C. over 4 hours. About 350 ml of water were collected during this time. The reactor was maintained at 190° C. for 3 hours. An additional 15 ml of water were collected and the reaction solution became bright yellow. The reaction solution was allowed to cool for 15 minutes and, then, the contents of the reactor were poured into an aluminum pan. A bright yellow, glassy solid was obtained upon cooling to room temperature. The product composition was determined by LC analysis. The product comprised only about 29.9% HETI-EG ester. Most of the other products were higher HETI condensation products, e.g. HETI condensed with HETI-EG ester, 2 HETI condensed with HETI-EG ester, HETI condensed with HETI, etc.

Preparing an ester of a functional imide by a conventional approach produces significant percentages of higher condensation products. The product distribution obtained from Comparative Example A, in which essentially stoichiometric amounts of HETI and ethylene glycol are used, shows only about 34.5% of the "expected" imide-ester and greater than 40% higher condensation products. Further, the imide-ester product is obtained with these higher condensates in a yellow, glassy mixture. An easily isolated and purified white, solid product is not produced.

The formation of higher condensation products is minimized by employing an excess of ethylene glycol in a modification of the conventional approach (Comparative Example B). A white solid product is obtained that comprises about 81.9% of the expected HETI-ester and less than 15% higher condensation products. However, this procedure still requires the separate preparation, isolation, and purification of the imide to be used as a starting precursor to the imide-ester.

Comparative Example C shows that significant amounts of higher condensation products are formed if nearly stoichiometric quantities of reactants are used in a one step process. Further, the product obtained is a glassy, yellow material.

Example 1 shows that ester formation at 180° C. is slow. Example 2 shows significant ester formation when the maximum reaction temperature is 200° C. Examples 3 and 4 show that longer reaction time gives more product. Example 5 shows that good yield of product is obtained whether the ethylene glycol is added early or late during the reaction. Example 6 shows that "seeding" the reaction mixture promotes product precipitation. Example 7 shows that using smaller excess of ethylene glycol increases the amount of higher HETI-ester condensation products. Example 8 shows that water is not necessary as an initial reaction medium. Example 9 shows that a large excess of ethylene glycol also produces a good yield of product.

COMPARATIVE EXAMPLE D

A 1-liter, glass resin kettle equipped with an overhead stirrer, steam-cooled condenser, water cooled condenser, nitrogen inlet and outlet, addition funnel, thermocouple, and external heating mantel was charged with 57.7 grams (0.30 mole) of trimellitic anhydride (TMA) and purged with nitrogen. About 100 ml of deionized water were then added to the kettle and stirring initiated. m-Xylylenediamine, 20.6 grams (0.152 mole) was added drop wise via the addition funnel over the span of about 2 minutes. The funnel was rinsed with 20 ml of water and the rinse was added also to the reactor. The reaction mixture was heated to about 50° C. Ethylene glycol (492 grams, 7.93 moles) was then slowly added via an addition funnel over the period of about an hour as the reaction temperature was increased to 90° C. The reaction mixture cleared to a very pale yellow solution during this time. The temperature was slowly raised to 132° C. over about an hour. Reflux began at around 130-132° C. and the reactor contents became cloudy. The reactor was maintained at 132° C. for 5 hours during which time a white precipitate formed. The reactor was allowed to cool to room temperature and the contents were filtered. The filter cake was washed twice with warm water and once with methanol. The recovered product weighed 59.5 grams after drying overnight at room temperature. The acid number of the product was 226 mg KOH/gram and corresponds closely to the theoretical value of 231.6 mg KOH/gram for N,N'-m-xylylene-bis-(trimellitimide). The product composition was determined by LC analysis that showed a purity of 98.7%. Analysis by $^1$H NMR shows about 96% of the bis-(trimellitimide) acid and 4% of the bis-(trimellitimide) ethylene glycol ester.

EXAMPLE 10

A 1-liter, glass resin kettle equipped with an overhead stirrer, steam-cooled condenser, water cooled condenser, nitrogen inlet and outlet, addition funnel, thermocouple, and external heating mantel was charged with 192.2 grams (1.0 mole) of trimellitic anhydride (TMA) and purged with nitrogen. About 300 ml of deionized water were then added to the kettle and stirring initiated. m-Xylylenediamine, 68.1 grams (0.500 mole) was added drop wise via the addition funnel over the span of about 7 minutes. The funnel was rinsed with 30 ml of water and the rinse was added also to the reactor. The reaction mixture was heated to about 90° C. and held at 90° C. for 1 hour. Ethylene glycol (355.2 grams, 5.72 moles) was then slowly added via an addition funnel over the period of about an hour. The temperature was raised to 195-200° C. over a period of about 5-6 hours and held at this temperature range for another 2.5 hours. A thick, creamy solid formed during this time. The reaction mixture was allowed to cool to room temperature and then mixed with 2.1 liters of water. A butter cream-like upper layer and a milky lower layer formed. The mixture was filtered and the filter cake was washed twice with warm (60° C.) water. A final methanol wash was conducted. After air-drying overnight at room temperature, 284 g of product was recovered. An acid number of 140 mg KOH/gram was measured. This acid number is consistent with a product mixture comprising about 60% N,N'-m-xylylene-bis-(trimellitimide) acid and 40% N,N'-m-xylylene-bis-(trimellitimide) ester.

Comparative Example D shows that a reaction temperature of about 130° C. will only very small amount of trimellitimide ester. Example 10 shows that a reaction temperature of around 200° C. will result in significant production of trimellitimide ester. Longer reaction time at 200° C. is expected to increase the yield of trimellitimide ester relative to trimellitimide acid.

Thus it is apparent that there has been provided, in accordance with the invention, a process that fully satisfied the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. A one step reaction process for the production of bis-trimellitimide ester monomers, comprising:
   reacting a 2:1 molar ratio of trimellitic anhydride and at least one diamine, and an excess of alcohol, or diol, or both,
   wherein said diamine is of the formula $H_2N$—X—$NH_2$, and X is selected from the group consisting of aliphatic, alicyclic, and aromatic, or a mixture of these.

2. The process of claim 1, wherein said reaction temperature is between about 160° C. to about 220° C.

3. The process of claim 1, wherein said excess of alcohol or diol is between 1.1-20 moles alcohol or diol to one mole of trimellitic anhydride or 0.5 mole diamine.

4. The process of claim 1, wherein water is added to said reaction creating an aqueous solution to aid in dispersing the reactants.

5. The process of claim 1, wherein said reaction time is about 1-8 hours.

6. The process of claim 4, wherein said aqueous solution is cooled, and said bis trimeilitie imide ester is precipitated as a solid.

7. The process of claim 6, wherein said solid is filtered or centrifuged.

8. The process of claim 1, wherein said diamine contains 2 to 16 carbon atoms.

9. The process of claim 8, wherein said diamine is selected from the group consisting of ethylenediainine; trimerhylenediamine, tetramethylenediamine: pentamethylenediamine; hexamethylenediamine; heptamethylenediamine; ocraniethylenediamine; 1,4-diaminocyclohexanti; 1,4-bis(aminomethyl)cyclohexane; bis-(4-aminocyclohexyl)methane; isophoronediamine; meta-xylylenediamine; para-xylylenediamine; 4,4'-diaminodiphenylinethane; 4,4'-diazninobiphenylpropane; 4,4'-diaminodiphenylsulfone; m-phenylenediamine; p-phenylenediarnine; 2,6-diaminonaphthalene; and 1,5-diaminonaphthalene.

10. The process of claim 1, wherein said dianiine is selected from the group consisting of ethylenedianiine; isophoronediamine; meta-xylylenediamine; and 4,4'-diarninodiphenylmethane and said excess of alcohol, diol, or both is ethylene glycol.

11. A copolymer of the product of claim 1 and polyamide.

12. The copolymer of claim 11 wherein said polyamide is at least one of nylon 6, nylon 6/6, nylon 6/10, nylon 11, nylon 12, nylon 6/12, nylon 10/12, nylon 4/6, nylon 6/9, or aramides selected from the group consisting of poly(m-phenylene iso-phthalamide), poly(p-phenylene ter-plithalamide), and poly(phthalamide), and copolymers based on these.

13. A copolymer of the product of claim 1 and at least one of polyethylene terephthalatc (PET), polybutylene terephthalate (PBT), poly(trimethylene) terephthalate (PTT), polyethylene isophthalate (PEI), and polyethylene naphthalate (PEN), or copolymers of these.

* * * * *